United States Patent [19]

Shabo

[11] Patent Number: 4,838,851
[45] Date of Patent: Jun. 13, 1989

[54] APPLICATOR AND PACKAGE THEREFOR

[76] Inventor: Alan L. Shabo, 10921 Wilshire Blvd., No. 1205, Los Angeles, Calif. 90024

[21] Appl. No.: 183,502

[22] Filed: Apr. 14, 1988

Related U.S. Application Data

[63] Continuation of Ser. No. 935,442, Nov. 26, 1986, abandoned.

[51] Int. Cl.⁴ .............................................. A61M 35/00
[52] U.S. Cl. ....................................... 604/1; 604/294; 132/320
[58] Field of Search ......................................... 604/1–3, 604/289, 290, 294, 310; 128/756; 132/88.7, D3, 82 A; 206/361–363; 401/209, 207; 15/244 R

[56] References Cited

U.S. PATENT DOCUMENTS

| | | | |
|---|---|---|---|
| 982,232 | 1/1911 | Bartholomew | 128/261 |
| 1,131,575 | 3/1915 | Tuttle . | |
| 2,469,399 | 4/1945 | Munson . | |
| 2,579,403 | 6/1950 | Slomowitz et al. . | |
| 2,902,146 | 5/1957 | Doherty . | |
| 3,005,543 | 4/1959 | Morse . | |
| 3,054,127 | 9/1962 | Petsch et al. | 15/244 R |
| 3,057,527 | 1/1963 | Bechtold | 604/294 |
| 3,103,682 | 9/1963 | Markle | 604/1 |
| 3,126,006 | 3/1964 | Dowell | 128/356 |
| 3,168,072 | 2/1965 | Nitta | 120/83 |
| 3,282,114 | 3/1966 | Pell . | |
| 3,324,849 | 6/1967 | Kravitz | 604/1 |
| 3,343,540 | 9/1967 | Siegel . | |
| 3,366,988 | 2/1968 | Menkin et al. | 15/244 R |
| 3,368,549 | 2/1968 | Barr et al. . | |
| 3,389,418 | 6/1968 | Senacabaugh | 604/289 |
| 3,508,547 | 4/1970 | Deuschle | 604/1 |
| 3,513,830 | 10/1970 | Kalaysian . | |
| 3,674,007 | 7/1972 | Freis . | |
| 3,757,782 | 9/1973 | Aiken . | |
| 3,759,375 | 9/1973 | Nappi . | |
| 3,776,220 | 12/1973 | Monaghan . | |
| 3,835,834 | 9/1974 | Brown . | |
| 3,863,654 | 2/1975 | Morane et al. | 132/88.7 |
| 3,890,204 | 6/1975 | Avery . | |
| 3,890,954 | 6/1975 | Greenspan . | |
| 3,896,808 | 6/1975 | Szpur . | |
| 3,923,604 | 12/1975 | Monaghan . | |
| 3,958,571 | 5/1976 | Bennington . | |
| 3,981,304 | 9/1976 | Szpur . | |
| 4,014,746 | 3/1977 | Greenspan . | |
| 4,037,975 | 7/1977 | Huffman | 401/6 |
| 4,096,864 | 6/1978 | Kletschka et al. | 128/354 |
| 4,192,300 | 3/1980 | Devers . | |
| 4,196,167 | 4/1980 | Olsen . | |
| 4,206,843 | 6/1980 | Rainey . | |
| 4,211,323 | 7/1980 | Olsen . | |
| 4,213,472 | 7/1980 | Gueret et al. | 132/887 |
| 4,291,697 | 9/1981 | Georgevich | 604/290 |
| 4,517,701 | 5/1985 | Stanford, Jr. | 15/106 |

Primary Examiner—C. Fred Rosenbaum
Assistant Examiner—Denise Whelton
Attorney, Agent, or Firm—Nilsson, Robbins, Dalgarn, Berlinger, Carson & Wurst

[57] ABSTRACT

An applicator for scrubbing an eyelid and a sealed, contaminant-excluding package therefor. The applicator includes an absorbent tip pre-wet for applying a liquid to an eyelid and affixed adjacent to a handle that is held firmly between the fingers for optimal control and safety near the eyeball.

9 Claims, 2 Drawing Sheets

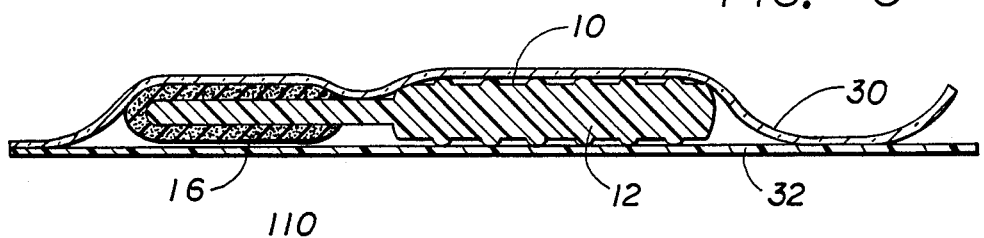
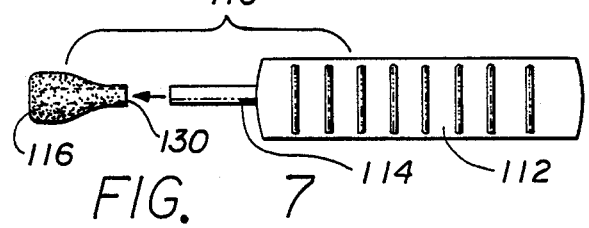
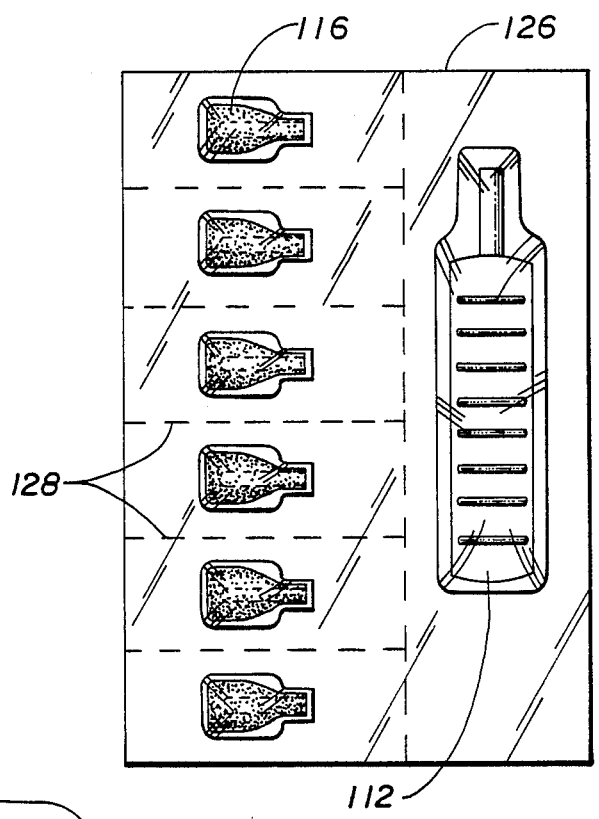
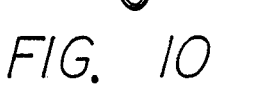
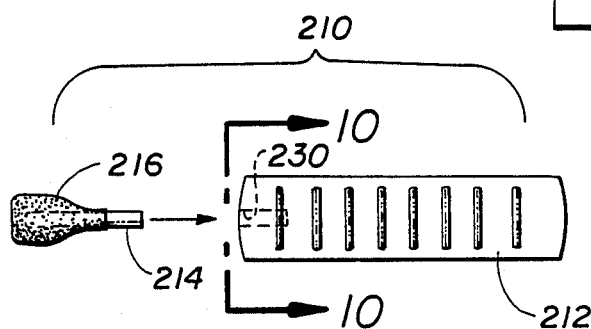

APPLICATOR AND PACKAGE THEREFOR

BACKGROUND OF THE INVENTION

This is a continuation of co-pending application Ser. No. 935,442 filed on Nov. 26, 1986 now abandoned.

A common, chronic or recurrent condition of the eye is inflammation of the eyelid margins, known medically as blepharitis. The condition is characterized by tenacious deposits on and around the eyelashes of an oily secretion (mild, simple blepharitis) and crusty desquamations or scales (seborrheic or squamous blepharitis). Blockage of the oil gland ducts at the eyelid margin may result in secondary infection with swollen, red-rimmed or ulcerated eyelids and styes (staphylococcal blepharitis). Blepharitis is particularly troublesome to contact lens wears when their contact lenses become coated and must be removed frequently for cleaning or replaced. In individuals with bacterial or viral conjunctivitis, there is often a pus or mucus discharge that causes the eyelids to stick together. Furthermore, in patients following eye operations, the eyelashes often become coated with medications or excessive discharge.

An important procedure in relieving such problems is cleansing of the eyelids to remove the deposits (oily secretion, scales pus, mucus and eye medications). Indeed, daily cleansing with a mild dilute soap solution is found to completely alleviate the milder forms of blepharitis. However, attempts to apply soap and scrub the eyelid using a cotton swab or a swab stick, such as is sold under the trademark Q-tip, can lead to some undersirable side effects or consequences. This is particularly true when attempting to remove extensive or tenacious discharge from the eyelid margins.

One undesirable and potentially dangerous side effect of using a cotton swab or swab stick is due to the fact that the thin stick of a cotton swab stick is difficult to hold firmly, particularly in close proximity to the eyeball. Due to its narrow, rounded shape, it tends to roll between the forefinger and thumb. Accordingly, the patient will often grasp the stick at its free end, with the consequent danger of poking the eye and scratching the cornea. Furthermore, the narrow, pointed tip of a cotton swab stick is difficult to apply directly to the eyelid margin. Patients often use the side of the cotton swab which causes the narrower tip to override the eyelid margin, further increasing the danger of scratching the cornea. Another undesirable side effect occurs when the patient uses the same swab or swab stick to remove discharge from both eyes. Since blepharitis is often associated with conjunctivitis, such practice can lead to transferring an infection from one eye to the other. In addition, a high concentration of soap can accidentally be applied to the eyelid, enter the tear fluid, and cause burning, stinging and possible damage to the sensitive corneal cells that line the eyeball and assist in vision. Finally, in scrubbing with cotton swabs not specifically made for application around the eye. filaments of cotton can loosen and become affixed to the eyelashes or actually shed into the inside of the eyelid causing irritation, infection and/or damage to the eyeball.

SUMMARY OF THE INVENTION

The foregoing problems are overcome by the present invention which provides an applicator designed specifically to scrub and to apply liquid to an eyelid, and a sealed, contaminant-excluding package for the applicator. The applicator is formed so as to provide controlled, safe moveent near the eyeball along the eyelid margin and to facilitate the application of liquid to the eyelid as well as the removal of tenacious deposits. In this regard, it comprises a generally flat handle formed to be grasped between the thumb and forefinger of the user. The handle has front and rear major surface joined by a minor, edge surface, the length and width of the handle being each substantially greater than its depth. An elongate peg extends outwardly from an edge of the handle and a swab is disposed on the peg adjacent the handly edge. The swab is formed of liquid absorbent material, and has a broad flat tip for optimal application to the eyelid margin. The swab is disposed so that the distance between the swab and the handle edge is substantially less than either the width or length of the handle. Preferably, the swab has greater width than depth, with the handle, peg and swab on a common longitudinal axis so that the plane of the swab lie substantially in the plane of the handle. The result is an applicator which can be easily grasped between the thumb and forefinger for optimal control of movement near the eyeball. When applied to the eyelid, the broad flat swab tip naturally angles properly close to the lash line to dispose liquid solution, such as a mild soap solution, and to remove tenacious deposits from the eyelid margin. Ridges or depressions can be formed so as to be exposed on major surfaces of the handle to further facilitate grasping between the thumb and forefinger. This, together with wrist movement to and fro, allows controlled movement back and forth along the eyelid margin without the danger of forward thrust toward the eyeball.

Preferably, the applicator is packaged with the desired liquid already absorbed in safe and proper concentration for use near the eyeball in the swab. By prepackaging the liquid with the swab, a single dose application can be provided for, so that the patient does not use the same swab on both eyes. It thus encourages the patient to use a separate swab for each eye, avoiding the transfer of conjunctivitis or other infection from one eye to the other. An antibacterial or antibiotic agent can be incorporated in the liquid.

In packaging the applicator, a sealed, contaminant-excluding packaging unit is provided. A blister pack can be used in which a flexible polymeric material is releasably sealed to a peel-away backing. The polymeric material of such a blister pack closely conforms to the shape of the applicator whereby to substantially isolate the handle from the swab. If any liquid does penetrate into the handle compartment, the flatness and thinness of the handle minimizes the adherence of liquid. In another embodiment, a plurality of swabs containing the liquid adsorbed therein are packaged along with a single handle, each separated from the other. Means are provided for removably connecting a selected swab to the handle as a disposable swab. After the swab is used, it is removed from the handle, and thereafter the handle is connected to another swab for use in the other eye or at another time. In this regard, the handle can be formed integrally with a peg and the swabs can be each formed with an opening for receiving the peg. Alternatively, each of the swabs can be disposed on the end of its own peg, which can be press-fit into an opening forming in the handle.

It will be appreciated that the inventive concepts herein have application not only to the medical treatment of blepharitis or other such conditions, but also to simple cosmetic use. For example, because the applicator is designed to be easily manipulated with respect to the eyelid, it can be used to remove eye makeup with minimum danger to the eye. The applicator can be provided as such without any liquid associated therewith, or it can be packaged with a liquid that facilitates removal of eye makeup. The construction of the applicator is quite economical, encouraging single dose usage, particularly when it is pre-packaged with the eye makeup removal liquid, therefore discouraging the use of the same swab on both eyes, and also discouraging the sharing of the swab among family members.

BRIEF DESCRIPTION OF THE DRAWINGS

FIG. 6 is a cross-sectional view of one of the package units of FIG. 5, taken along line 6—6 of FIG. 5;

FIG. 7 is a plan, exploded view of an applicator formed in accordance with the second embodiment of the invention;

FIG. 8 is a package of the applicator handle of FIG. 7 and six swabs of FIG. 7;

FIG. 9 is a plan, exploded view of an applicator formed in accordance with another embodiment of the invention; and FIG. 10 is an elevational view of the front of the applicator handle of FIG. 9, taken on line 10—10 of FIG. 9.

DETAILED DESCRIPTION

Figure 1:
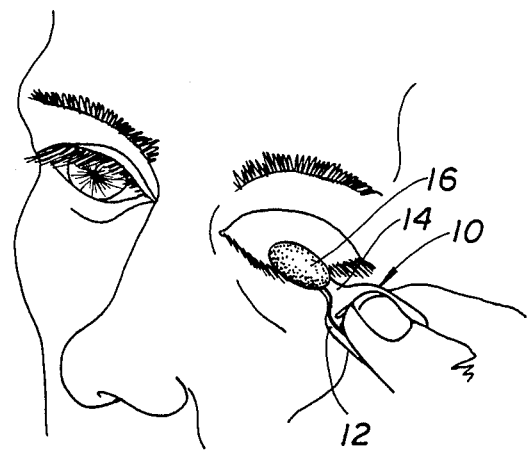
FIG. 1 illustrates use of an applicator of the present invention to scrub and to apply liquid on a patient's eyelid.

Referring to FIG. 1, use of the applicator 10 is shown. The applicator 10 includes a handle formed with an elongate peg 14 on which is disposed a swab 16 in flattened form with rounded corners. The applicator is applied so that the swab lies flat on the eyelid, a position which is facilitated by the arrangement of the components as will be described in more detail hereinafter.

Figure 2A:
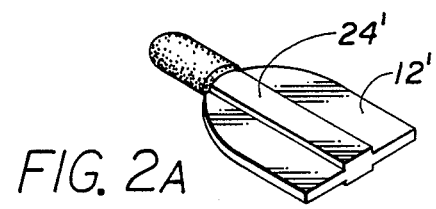
FIG. 2A is an alternate embodiment of the applicator.
Figure 2:
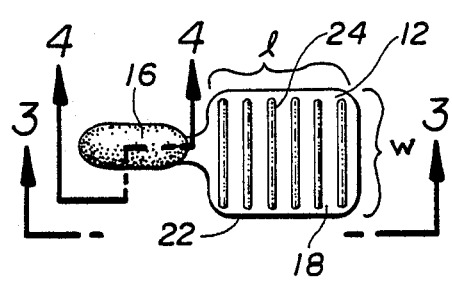
FIG. 2 is a plan view of an applicator formed in accordance with the first embodiment of the present invention.
Figure 3:
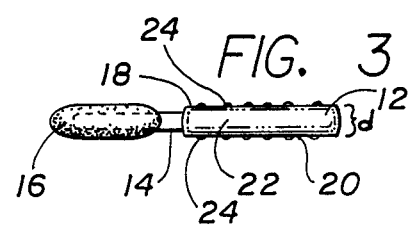
FIG. 3 is an elevational view of the applicator, taken on line 3—3 of FIG. 2.

A first embodiment of the applicator is illustrated in FIGS. 1 through 6. Referring to FIGS. 2 and 3, the handle 12 of the applicator is formed with front and rear major surfaces 18 and 20 joined by a minor, edge surface 22. As indicated by the letters "l" and "w" in FIG. 2 and "d" in FIG. 3, the length and width of the handle 12 are each substantially greater than its depth. A plurality of ridges 24 are formed on the major surfaces of the handle, either on one side, or on both sides as shown, to facilitate the ability to grasp the handle between the thumb and forefinger. In place of ridges 24, one can use grooves.

FIG. 2A illustrates an alternate embodiment wherein the generally flat handle 12' is formed with a raised central region 24' on each side (only one side being shown in the drawing).

Figure 4:
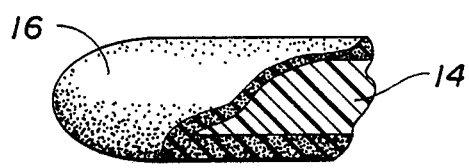
FIG. 4 is an elevational view, partially in cross-section, of the applicator tip, taken approximately on line 4—4 of FIG. 2.

As shown in shadow in FIG. 3, the peg 14 is elongate and extends outwardly from the edge 22 of the handle 12. Referring additionally to FIG. 4, the swab 16 is disposed on the peg 14 so as to lie adjacent to the edge 22 of the handle 12. The swab can be formed of any liquid absorbent material, for example, a porous sponge material, or a cotton backing.

As shown in FIGS. 2 and 3, the swab 16 has greater width than depth, and is disposed on a common longitudinal axis so that the plane of the swab lies substantially in the plane of the handle. Also, in the embodiment of FIGS. 1–6, as shown, the length dimension of the handle is less than twice the width dimension thereof. This facilitates use of the applicator to scrub and apply liquid near the eye as one unit for optimal control of movement.

Figure 5:
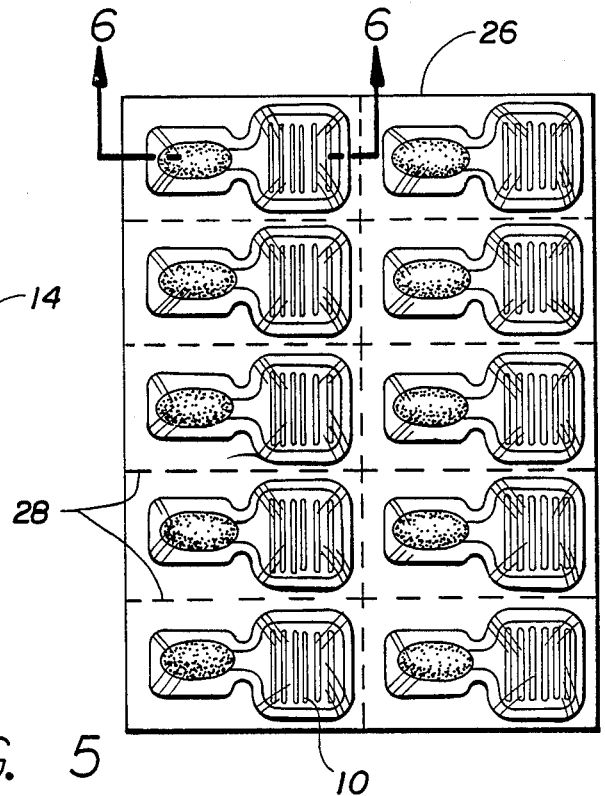
FIG. 5 is a plan view of a blister pack package of ten applicators.

Referring to FIG. 5, a blister-pack package 26 of applicators 10, is shown. This particular package accommodates ten applicators 10, with liquid absorbed in the swab 16, each in its individual sealed, contaminant-excluding packaging unit defined by tear lines of weakness 28. Referring to FIG. 6, an individual unit is shown in cross-section in which a blister pack, flexible polymeric material 30 is releasably sealed to a peel-way paper backing 32 so as to encase an applicator 10. The polymeric material closely conforms to the shape of the applicator so as to substantially isolate the handle 12 from the swab 16. As shown in FIG. 6, this isolation is facilitated by coaction of at least one ridge with the closely conformed polymeric material. Because of the unique shape of the handle 12, even if liquid were to run off from the swab 16 and migrate into the handle 12 compartment, only minimum wetting of the handle would occur. The generally flat surfaces together with the ridges or grooves on the major surface would facilitate grasping even when the handle was wet.

Referring to FIG. 7, there is shown an applicator 110 constructed in accordance with another embodiment. The applicator 110 includes a handle 112 that is substantially more elongated than the handle 12 of the embodiment of FIGS. 1–6. It is formed at one edge with an integral peg 114 which is designed to fit into a disposable swab 116. The swab 116 is formed of a sponge-like material having an opening 130 at one end to receive the peg 114.

The peg 114 can be oval-shaped to match an oval-shaped opening in the swab 116 so as to ensure that the swab 116 is oriented in a plane substantially in the plane of the handle 112.

Referring to FIG. 8, a sealed, contaminant-excluding package is shown in which a plurality of swabs 116 are each contained in its own blister pack unit. The swab tips include a liquid, such as a mild soap solution, absorbed therein. While a plurality of swabs 116 are provided, a single handle 112 is provided encased in its own blister pack compartment. The result is a package 126 in which the individual swabs are sequentially removable by means of tear lines of weakness 128. This package has the advantage of tremendous economy as the swab are disposable following single eyelid application while the handle is reusable.

Referring to FIGS. 9 and 10, there is shown an applicator 210 formed in accordance with still another embodiment of the invention. In this embodiment, the handle 212 is also more elongated than in the handle 12 of the embodiment of FIGS. 1–6, but is not formed integrally with a peg. Rather, a peg 214 is connected directly to each swab 216 so as to be an integral part thereof. This construction is particularly useful when it is desired to use cotton batting closely wound around the peg 214. In this case, the handle 212 is formed with an opening 230, shown in shadow in FIG. 9, into which the peg 214 can be press-fit.

The peg 114 or 214 can be oval-shaped to match an oval-shaped opening in the swab 216 so as to ensure that the swab is oriented in a plane substantially in the plane of the handle 212.

In common with all of the illustrated embodiments, as shown in the drawing, the handle is thicker on at least a portion of the longitudinal axis than along the handle edge. Such thickness is provided by one or more ridges 24 as in FIGS. 2, 7, and 9, or by the raised central portion 24' in FIG. 2A. Such structure facilitates the above-described controlled, safe movement of the applicator near the eyeball along the eyelid margin so that a scrubbing action can be safely accomplished.

It will be appreciated that modification can be made within the spirit of the appended claims. For example, one could construct the applicator with multiple pegs and swabs extending from one or more of the handle edges in addition to the peg and swab described in the illustrated embodiment.

I claim:

1. An applicator for scrubbing, and for applying a liquid to an eyelid, comprising:
    a thin, one-piece handle formed to be grasped between the thumb and forefinger of a user and having front and rear major surfaces joined by a minor, edge surface;
    a peg extending outwardly entirely perpendicularly from a first edge of said handle horizontally axially thereof; and
    a swab on said peg adjacent said handle edge, formed of liquid absorbent material;
    said swab, said handle and said peg each having a length dimension defining the horizontal axis of the applicator, a width dimension in a first plane and a thickness dimension transverse of said first plane, the length and width of the handle being each substantially greater than its thickness, the length of the handle being substantially greater than its width the distance between said swab and said handle edge being substantially less than either width or length of said handle, the thickness dimension of said handle being greater than the thickness dimension of said peg, and the width of said handle being greater than the width of said swab, said swab having greater length and width than thickness and greater length than width.

2. The applicator of claim 1 including a plurality of ridges exposed on the major surfaces of said handle.

3. The applicator of claim 1 including a liquid absorbed in said swab.

4. The applicator of claim 1 in which the length dimension of said peg is coaxial with the length dimension of said handle.

5. The applicator of claim 1 in which said handle is thicker on at least a medial portion thereof than along an edge thereof.

6. The applicator of claim 1 in which the length of the handle is less than twice its width whereby to permit a user to freely grasp the handle between the user's thumb and forefinger adjacent said first handle edge.

7. The package of claim 1 in which said swabs, said pegs and said handle hole are each formed with a greater width than thickness, said hole, pegs and swabs being oriented so as to dispose each swab with its plane lying substantially in the plane of said handle.

8. A sealed, contaminant-excluding packaging including components of an applicator, said components comprising:
    a handle having a length dimension defining its longitudinal axis, formed to be grasped between the thumb and forefinger of a user and having front and rear major surfaces joined by a minor, edge surface, the length and width of the handle being each substantially greater than its thickness;
    a plurality of swabs formed of liquid absorbent material containing a liquid absorbed therein; and
    means for removably connecting a selected swab to said handle as a disposable swab comprising a plurality of elongate pegs, each peg formed to extend outwardly from said handle edge along the longitudinal axis of said handle, each of said swabs being disposed on the end of a said peg;
    said handle and each of said swabs being separately encased in packaging material, said handle having a hole formed through its edge into its body for successively removably receiving each of said pegs;
    said packaging material being formed with lines of weakness permitting successive separations of encased swabs therefrom.

9. A sealed, contaminant-excluding package including components of an applicator, said components comprising:
    a handle having a length dimension defining its longitudinal axis, formed to be grasped between the thumb and forefinger of a user and having front and rear major surfaces joined by a minor, edge surface, the length and width of the handle being each substantially greater than its thickness;
    a plurality of swabs formed of liquid absorbent material containing a liquid absorbed therein; and
    means for removably connecting a selected swab to said handle as a disposable swab comprising at least one elongate peg formed to extend outwardly from said handle edge along the longitudinal axis of said handle;
    said handle and each of said swabs being separately encased in packaging material;
    said packaging material being formed as a blister pack of a flexible polymeric material with lines of weakness permitting successive separations of encased swabs therefrom, said polymeric material being releasably sealed to a peel-away backing and closely conforming to the shape of said handle and said swabs whereby to substantially isolate said handle from said swabs.

* * * * *

UNITED STATES PATENT AND TRADEMARK OFFICE
CERTIFICATE OF CORRECTION

PATENT NO. : 4,838,851
DATED : June 13, 1989
INVENTOR(S) : Alan L. Shabo

It is certified that error appears in the above-identified patent and that said Letters Patent is hereby corrected as shown below:

Col. 1, line 18, delete "wears" and insert --wearers--.

Col. 1, line 26, insert a comma after "scales".

Col. 2, line 1, delete "moveent" and insert --movement--.

Col. 2, line 6, delete "surface" and insert --surfaces--.

Col. 2, line 11, delete "handly" and insert --handle--.

Col. 2, line 18, delete "lie" and insert --lies--.

Column 2, line 64, delete "forming" and insert --formed--.

Signed and Sealed this

Fourteenth Day of May, 1991

Attest:

HARRY F. MANBECK, JR.

*Attesting Officer*  *Commissioner of Patents and Trademarks*